(12) United States Patent
Lauritzen et al.

(10) Patent No.: US 9,017,711 B2
(45) Date of Patent: Apr. 28, 2015

(54) SOFT TISSUE WRAP

(75) Inventors: Nels J. Lauritzen, Piscataway, NJ (US);
Abdulhafez A. Selem, Cliffwood, NJ
(US); Lawrence A. Shimp, Morganville,
NJ (US); Hsiu Ying Sherry Wang,
North Brunswick, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 216 days.

(21) Appl. No.: 13/096,570

(22) Filed: Apr. 28, 2011

(65) Prior Publication Data

US 2012/0276150 A1 Nov. 1, 2012

(51) Int. Cl.
| | | |
|---|---|---|
| *A61F 2/00* | (2006.01) | |
| *A61K 9/70* | (2006.01) | |
| *A61K 35/32* | (2006.01) | |
| *A61K 38/39* | (2006.01) | |
| *A61K 38/18* | (2006.01) | |
| *A61L 27/24* | (2006.01) | |
| *A61L 27/32* | (2006.01) | |
| *A61L 27/36* | (2006.01) | |
| *A61L 27/56* | (2006.01) | |

(52) U.S. Cl.
CPC .................. *A61K 38/39* (2013.01); *A61K 38/18* (2013.01); *A61L 27/24* (2013.01); *A61L 27/32* (2013.01); *A61L 27/3662* (2013.01); *A61L 27/3687* (2013.01); *A61L 27/56* (2013.01); *A61L 2300/414* (2013.01); *A61L 2430/34* (2013.01)

(58) Field of Classification Search
USPC ....................................................... 424/444
See application file for complete search history.

(56) References Cited

U.S. PATENT DOCUMENTS

| | | | |
|---|---|---|---|
| 4,127,902 A | 12/1978 | Homsy | |
| 4,733,850 A | 3/1988 | Thompson | |
| 5,219,895 A | 6/1993 | Kelman et al. | |
| 5,595,621 A | 1/1997 | Light et al. | |
| 5,681,353 A | 10/1997 | Li et al. | |
| 6,838,493 B2 | 1/2005 | Williams et al. | |
| 6,852,330 B2 | 2/2005 | Bowman et al. | |
| 6,884,428 B2 | 4/2005 | Binette et al. | |
| 6,984,241 B2 | 1/2006 | Lubbers et al. | |
| 6,991,643 B2 | 1/2006 | Saadat | |
| 7,179,883 B2 | 2/2007 | Williams et al. | |
| 2003/0078659 A1 | 4/2003 | Yang | |
| 2003/0099762 A1* | 5/2003 | Zhang et al. | 427/2.1 |
| 2003/0118560 A1 | 6/2003 | Kelly et al. | |
| 2005/0220848 A1* | 10/2005 | Bates | 424/443 |
| 2007/0250114 A1 | 10/2007 | Drapeau | |
| 2008/0069852 A1* | 3/2008 | Shimp et al. | 424/423 |
| 2009/0157193 A1* | 6/2009 | McKay | 623/23.72 |
| 2009/0312524 A1 | 12/2009 | Lauritzen | |

FOREIGN PATENT DOCUMENTS

| | | |
|---|---|---|
| WO | 03007847 A1 | 1/2003 |
| WO | 2006089267 A2 | 8/2006 |
| WO | 2007082088 | 7/2007 |
| WO | 2007087353 | 8/2007 |

OTHER PUBLICATIONS

International Search Report for Application No. PCT/2008/085408 mailed Apr. 6, 2009.

* cited by examiner

*Primary Examiner* — Michael B Pallay
(74) *Attorney, Agent, or Firm* — Sorell Lenna & Schmidt LLP

(57) ABSTRACT

Compositions and methods for treating and healing injured soft tissues such as tendons and ligaments are provided. The composition may be a wrap comprising human collagen in the form of a sheet. The human collagen has been processed so that is retains proteins that are associated with it in its natural state. The sheet may optionally be coated on one or more sides with one or more of additional human collagen, therapeutic agents, additional soft tissue growth factors or hydroxyapatite.

11 Claims, No Drawings

SOFT TISSUE WRAP

BACKGROUND

As the world population has been aging and trying to remain more active, there has been an increased prevalence of damage not only to bones, but also to soft tissues. Damage to soft tissue can lead to decreased mobility and increased pain. Therefore, repair and healing of soft tissue is important. Two of the types of soft tissue with respect to which repair and healing are particularly important are tendons and ligaments.

Tendons are specialized connective tissue that connect and attach muscles to bones. Tendons transmit tensile loads from muscles to the attached bones, thereby causing movement of the bones around joints. In order to accomplish their desired function, tendons must be able to sustain high tensile forces, but they also must be flexible enough to bend around bony surfaces.

Ligaments are also specialized connective soft tissues. They connect and attach bones to other bones. Ligaments provide stability to joints by being flexible enough to allow natural movement of the bones, yet also by being strong and inextendible, thereby preventing resistance to applied forces. Thus, in order for bones and muscles to function properly, tendons and ligaments need to be able to function properly as well.

In both tendons and ligaments, bundles of collagen fibers are embedded in a connecting matrix that may be referred to as a ground substance. The collagen usually consists mainly of Type I collagen fibers. These bundles of collagen fibers provide the load carrying elements, and they are aligned to resist the applied tensile loads. In tendons, the collagen fibers are arranged in nearly parallel formation, thereby enabling them to withstand high unidirectional loads. In ligaments, the collagen fibers are arranged in a less parallel formation, thereby enabling them to withstand predominant tensile stresses in one direction and smaller stresses in other directions. Both tendons and ligaments contain cells in low density occurrence in relation to the extracellular matrix in which they reside. Unfortunately, this low density provides them with a limited capacity for healing when injured. Small tears can heal by themselves, but larger tears require surgical intervention in the form of suturing, and in the case of tendons, complete breaks often require replacement of the tendon itself.

Additionally, very often the healing process results in the formation of scar tissue, which consists of non-aligned fibers. Typically scar tissue forms with a large type III collagen component, and it is much weaker than the original tissue.

Given the importance of tendons and ligaments, there is concern that when they tear or deteriorate, persons with the damaged tissue will suffer decreased mobility and increased pain. The present application provides compositions and methods that may be used to assist in the repair or healing of these tissues.

SUMMARY

The present application provides compositions and methods for facilitating repair and healing of soft tissue. Through the use of various embodiments of the present application, one may enable tissues such as tendons and ligaments to have a quicker and more efficient recovery from damage or deterioration.

In some embodiments, there is a soft tissue wrap comprising collagen and conserved natural growth factors, wherein the collagen and conserved natural growth factors are derived from a human or recombinant animal source and the collagen is cross-linked and is in the form of a sheet that is at least 50% porous. A conserved growth factor is one that is associated with the collagen when the collagen is in its naturally occurring state, and it is also associated with the collagen by the same types of bonds after processing, and thus does not change form during processing. This collagen that has conserved growth factors may also be referred to as "normal collagen" or "active collagen." In some embodiments the wrap consist of human collagen, and in other embodiments, it may also or alternatively comprise collagen from a human compatible recombinant animal source that has conserved growth factors as well as animal collagen with enzymatically removed proteoglycan groups (by enzymes such as is described in U.S. Pat. No. 6,455,309 and related patents, the disclosures of which are incorporated by reference). In some embodiments, the collagen, which is in the form of collagen fibrils, i.e., triple helix form, retains that form. The collagen may be completely unmodified or modified in a manner that does not destroy the integrity of the triple helix form. For example, the end groups of the collagen fibers may be removed by specific enzymes (as opposed to general protease enzymes) and the collagen fibers can then be broken down to fibrils to make a suspension that is then reassembled later if desired.

In some embodiments, the present application provides a method for making a soft tissue wrap comprising: subjecting human collagen (or collagen from a recombinant animal source or enzymatically modified animal source) to an acid suspension; exposing the human collagen to formaldehyde or other cross-linking agent thereby causing the human collagen to cross-link; and forming a sheet from the human collagen; wherein the human collagen has not been exposed to any enzymes that are capable of removing or denaturing soft tissue growth factors that are associated with the human collagen. This processing technique allows the growth factors to be conserved. Other chemicals that may be used in the processing of the collagen instead of or in combination with formaldehyde include but are not limited to gluteraldehyde and natural cross-linking materials such as sugar based materials (e.g., a sugar-protein complex) and genipin.

In various embodiments, the present application may take advantage of the fact that human collagen is immune privileged in humans. The phrase "immune privileged" means that it will not induce an immunologically adverse response in the host into which it is introduced. Thus, in some embodiments, by avoiding enzyme treatments, high pH and oxidizing treatments, the naturally occurring proteins that are associated with collagen in its naturally occurring state may be conserved and the recipient organism will not mount an immunological response to the wrap. This combination of factors can greatly facilitate healing and repair of soft tissue. In some embodiments, the collagen is not immunogenic.

In various embodiments of the present application, different collagen containing tissue can be used as sources of the collagen. In some embodiments, particularly those in which the wrap is intended to be used for tendons, preferably a tendon or other connective tissue source in combination with collagen from a tendon are used.

Additional features and advantages of various embodiments will be set forth in part in the description that follows, and in part will be apparent from the description, or may be learned by the practice of various embodiments. The objectives and other advantages of various embodiments will be realized and attained by means of the elements and combinations particularly pointed out in the description and appended claims.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

The numerical values set forth in the specific examples are reported as precisely as possible. Any numerical value, however, inherently contains certain errors necessarily resulting from the standard deviation found in the respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the application. While the application will be described in conjunction with the illustrated embodiments, it will be understood that the embodiments are not intended to limit the application. On the contrary, the application is intended to cover all alternatives, modifications, and equivalents that may be included within the application as defined by the appended claims.

Additionally, the headings below are not meant to limit the disclosure in any way; embodiments under any one heading may be used in conjunction with embodiments under any other heading.

DEFINITIONS

It is noted that, as used in this specification and the appended claims, the singular forms "a," "an," and "the," include plural referents unless expressly and unequivocally limited to one referent.

The term "practitioner" or "user" means a person who is using the methods and/or devices of the current disclosure on the patient. These terms includes, without limitation, doctors (e.g., surgeons, interventional specialists, and physicians), nurses, nurse practitioners, other medical personnel, clinicians, veterinarians, or scientists. The various embodiments of the present application may be used by practitioners.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

"Treating" or "treatment" of a disease or condition refers to executing a protocol, which may include the use of the devices and methods herein and/or administering one or more wraps or sheets to a patient (human, normal or otherwise, or other mammal), in an effort to alleviate signs or symptoms of a disease or to facilitate in the repair or healing of tissue. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient.

Preferred Embodiments

In one embodiment, the present application provides a soft tissue wrap comprising human collagen. The human collagen is cross-linked and in the form of a sheet that is in some embodiments at least 50% porous. The collagen has associated with it one or more conserved proteins, which refer to proteins that are associated with the collagen when the collagen is in its naturally occurring state. The proteins may for example include soft tissue growth factors. The collagen, which retains native growth factors, may be referred to as active collagen, which may be derived from human or human compatible animal sources (such as genetically engineered pigs) and has been processed without damaging protease enzyme treatments or other physical or chemical treatments that will remove or denature all of the native growth factors, e.g., certain base treatments (the growth factors are generally acid stable). Because the soft tissue growth factors retain their form and association with the collagen, they are referred to as conserved.

The collagen may have the same composition as in naturally occurring sources. Examples of sources of collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen may further or alternatively comprise hetero- and homo-trimers of any of the above-recited collagen types. In some embodiments, the collagen comprises hetero- or homo-trimers of human collagen type I, human collagen type II, human collagen type III, or combinations thereof. In some embodiments, the collagen is all type I or substantially all is collagen type I, e.g., at least 60%, at least 65%, at least 70%, at least 75%, at least 80%, at least 85%, at least 90%, or at least 95%.

In some embodiments all soft tissue growth factors are conserved. In other embodiments, at least 50%, at least 55%, at least 60%, at least 65%, at least 70%, at least 75%, at least 80% at least 85%, at least 90%, at least 95%, or at least 99% of the tissue growth factors are conserved.

The collagen may be from any collagen containing organ source such as skin, fascia, intestine, tendon, bladder and trachea. In some embodiments, human compatible collagen, and xenograft collagen can be used if they can be rendered non-immunogenic by a process that does not destroy the activity of the natural growth factors contained in the tissue or diminishes the activity by an acceptably small amount. Examples of processes that conserve natural growth factors include but are not limited to glycosidase digestion of carbohydrate moieties of the xenograft, which are optionally followed by treatment of carbohydrate moieties of the xenografts with a capping agent. Thus, sugars and other substances may be removed during processing, while the soft tissue growth factors remain associated with the collagen. In some embodiments soft tissue growth factors are conserved, but any sugars have been removed or at least 50%, at least 55%, at least 60%, at least 65%, at least 70%, at least 75%, at least 80% at least 85%, at least 90%, at least 95%, or at least 99% of them have been removed.

In some embodiments, the sheet is between 0.5 mm and 10 mm thick. In other embodiments, the sheet is between 1 mm and 3 mm thick. In still other embodiments, the sheet is between 1.5 mm and 2.5 mm or between 2.5 mm and 3.5 mm or between 3.5 mm and 4.5 mm thick. The thickness is measured when the sheet is laid flat.

The soft tissue wrap may have varying degrees of porosity, e.g., at least 50%, at least 60%, at least 70%, or at least 80%. In some embodiments, the porosity is up to 60%, up to 70%, up to 80% or up to 90% of the sheet. The pores may be formed as the fibers condense out of the water based suspension during a drying process. The concentration of the pores may be increased during the drying cycle. Optionally, the sheet can be compressed either before or after cross-linking in order to reduce porosity. If compressed before cross-linking, there is lower porosity than if the compression occurs after cross-linking.

The growth factors include osteoinductive agents (e.g., agents that cause new bone growth in an area where there was none) and/or osteoconductive agents (e.g., agents that cause ingrowth of cells) and also fibrous or soft tissue inducing agents. Osteoinductive agents can be polypeptides or polynucleotide compositions. Polynucleotide compositions of the osteoinductive agents include, but are not limited to, isolated Bone Morphogenic Protein (BMP), Vascular Endothelial Growth Factor (VEGF), Connective Tissue Growth Factor (CTGF, which may be specific for tendons and ligaments), Osteoprotegerin, Growth Differentiation Factors (GDFs), Cartilage Derived Morphogenic Proteins (CDMPs, which can be a foundation for soft or hard tissue), Lim Mineralization Proteins (LMPs), Platelet derived growth factor, (PDGF or rhPDGF, which is particularly advantageous for use with soft tissue), Insulin-like growth factor (IGF) or Transforming Growth Factor beta (TGF-beta) polynucleotides.

The soft tissue wrap may also comprise one or more additional growth factors, including but not limited to rhBMP12 or BMP7. These additional growth factors, unlike the conserved proteins are ones that have been added to the collagen during a subsequent processing step. The identity of proteins may be the same as or different than the conserved proteins. In some embodiments the collagen may be treated so that it also binds to these additional proteins. In other embodiments, these additional proteins are not bound to the collagen, but are loosely associated with the collagen. In some embodiments, the resulting concentration of growth factors is from 10% to 30% greater than in the natural state or from 30% to 50% greater than in the natural state or from 50% to 70% greater than in the natural state.

In addition to including soft tissue factors that have the same identity as one or more of the conserved soft tissue growth factors noted above, the additional growth factors include polynucleotide compositions. Polynucleotide compositions include, but are not limited to, gene therapy vectors harboring polynucleotides encoding the osteoinductive polypeptide of interest. Gene therapy methods often utilize a polynucleotide that codes for the osteoinductive polypeptide operatively linked to or associated with a promoter or any other genetic elements necessary for the expression of the osteoinductive polypeptide by the target tissue. Such gene therapy and delivery techniques are known in the art (see, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, to promote or to facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties.

Gene therapy vectors further comprise suitable adenoviral vectors including, but not limited to for example, those described in U.S. Pat. No. 5,652,224, which is herein incorporated by reference.

Additional growth factors also include but are not limited to isolated polynucleotides that encode Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents also include, but are not limited to, full length proteins, fragments or variants thereof.

Variants of the isolated osteoinductive agents include, but are not limited to, polypeptide variants that are designed to increase the duration of activity of the osteoinductive agent in vivo. Typically, variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that may be included within the wrap are typically sterile. In a non-limiting method, sterility is readily accomplished for example by filtration through sterile filtration membranes (e.g., 0.2 micron membranes or filters). In one embodiment, the matrix includes osteoinductive agents comprising one or more members of the family of Bone Morphogenic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents may comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents that are included in the wrap include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors that can be loaded in the wrap further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents that can be loaded in the matrix include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents that can be loaded in the wrap include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents that can be loaded in the wrap include one or more members of the family of Transforming Growth Factor-beta ("TGF-betas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents that can be loaded in the wrap include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BCO30959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BCO28237 or AAH28237, as well as mature GDF-10 polypeptides or polynucleotides encoding the same. GDF-11 polynucleotides or polypeptides corresponding to GenBank Accession Numbers AF100907, NP_005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP_004855, as well as mature GDF-15 polypeptides or polynucleotides encoding the same.

In another embodiment, isolated osteoinductive agents that can be loaded in the wrap include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents that can be loaded in the matrix include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents that can be loaded in the matrix include one or more members of any one of the families of Bone Morphogenic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), as well as mixtures or combinations thereof.

In another embodiment, the one or more isolated osteoinductive agents that can be loaded in the wrap are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and/or any combination thereof; Osteoprotegerin; TGF-beta-1, TGF-beta-2, TGF-beta-3, or any combination thereof; or any combination of one or more members of these groups.

In some embodiments, the ligand is BMP-2, BMP-7 and/or GDF-5 and may be used at 1-2 mg/cc of matrix. The concentrations of ligand can be varied based on the desired length or degree of osteogenic effects desired. However, the optimum ratio of ligand to receptor should be from about 0.5 to about 1.5 or from about 0.7 to about 1.0 so that the ligand works with optimum efficacy.

The soft tissue wrap may further comprise a second source of human collagen. The second source of human collagen may be derived from the same tissue as collagen that is used to form the sheet. However, this second source may have been processed to have one or more proteins that are associated with it in its naturally occurring state removed. Thus, in these embodiments, it is not bound to conserved proteins. In some embodiments, at least substantially all of these proteins, if not all of these have been removed from this second source of collagen. In other embodiments, this second source of collagen is a useful source of additional growth factors.

In some embodiments, optionally the collagen sheet is treated with another activated collagen. The treatment may be carried out after cross-linking of the collagen within the collagen sheet. The additional activated collagen is collagen that is derived from a human or engineered animal to render it human compatible. This additional collagen may be activated by making it into a suspension without the use of an enzyme treatment or high pH, which would correspond to a strong base. The collagen suspension may then be applied to the collagen membrane by, for example, painting the suspension on the surface and letting it dry, using the collagen membrane (which is the sheet) as a filter and putting the liquid through with a vacuum so that the liquid is removed and the suspension is trapped in the pores in the membrane. Thus, there may be two sources of active collagen. Because cross-linking can be damaging to growth factors, the second collagen source, which is not cross-linked, may have a higher growth factor content.

In other embodiments, a suspension of activated collagen is applied to a mesh of collagen or sheet of collagen that is not activated. Thus, in these embodiments, the collagen to which the suspension is applied does not contain conserved proteins.

In some embodiments, the soft tissue wrap may further comprise a nano-hydroxyapatite coating. This component may be sprayed onto the sheet. In some embodiments, the amount of nano-HA coating it 0.5 to 90% by weight, preferably 0.5% to 5.0% by weight.

In some embodiments, the soft tissue wrap may further comprise a mesh structure or a sponge. In some embodiments, the mesh structure or sponge is located on only one side of the sheet. The thickness of the mesh structure or sponge may be 0.5 mm to 2 mm, or 2 mm to 4 mm. The sponge may be made of collagen and the mesh allows cell infiltration, which helps remodeling and tissue growth. The dense side may be a collagen film of significantly lower porosity that may function to discourage non-collagen cells from migrating to a wound site.

In some embodiments, the soft tissue wrap may further comprise demineralized bone particles, which in some embodiments are present in a weight concentration of 5-90%; 10-25%; 30-45%; 50-75: or 80-90%. The demineralized bone particles can help to grow collagen tissues in low oxygen environments such as those found in a tendon/ligament. Demineralized bone particles can also help to anchor an implant to a site of interest. However, in embodiments such as those associated with a small tendon, e.g., the finger, one should be cautious to avoid mineralizing the tendon and in some embodiments use no demineralized bone particles.

In some embodiments, the soft tissue wrap may further comprise a therapeutic agent selected from the group consisting of a growth factor, a cytokine, a statin, an anti-inflammatory agent, a steroid, an analgesic, antibiotic, an anti-infiltrating agent, and a combination thereof. Preferably, when one or more of these agents is used, a therapeutically effective amount will be used.

The wrap may also comprise resorbable or non-resorbable polymers or combinations thereof (especially in the form of threads or a mesh to mechanically reinforce the wrap). Examples of resorbable polymers include, but are not limited to, poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphazenes, collagen, elastin, silk, cellulose starch, chitosans, gelatin, alginates, cyclodextrin, polydextrose, dextrans, vinylpyrrolidone, polyvinyl alcohol (PVA), PVA-g-PLGA, polyethyleneglycolterephtalate and polybuthylene-terephtalate (PEGT-PBT) copolymer (polyactive), methacrylates, poly(N-isopropylacrylamide), polyethylene oxides (as known as polyoxyethylene or PEO), poly-propylene oxide (also known as polyoxypropylene or PPO), poly(aspartic acid) (PAA), PEO-PPO-PEO (Pluronics™, BASF), PEO-PPO-PAA copolymers, PLGA-PEO-PLGA, polyphosphoesters, polyanhydrides, polyester-anhydrides, polyamino acids, polyurethane-esters, polyphosphazines, polycaprolactones, polytrimethylene carbonates, polydioxanones, polyamide-esters, polyketals, polyacetals, glycosaminoglycans, chondroitin sulfate, hyaluronic acid, hyaluronic acid esters, polyethylene-vinyl acetates, silicones, polyurethanes, polypropylene fumarates, polydesaminotyrosine carbonates, polydesaminotyrosine arylates, polydesaminotyrosine ester carbonates, polydesaminotyrosine ester arylates, polyorthocarbonates, polycarbonates, or copolymers or physical blends thereof or combinations thereof. In some embodiments the polymers are present in an amount of 5%-90% or 20%-40% by weight.

Non-resorbable polymers can include, but are not limited to, polyethylene, delrin, silicone, polyurethane, copolymers of silicone and polyurethane, polyolefins such as polyisobutylene and polyisoprene, acrylamides such as polyacrylic acid and poly(acrylonitrile-acrylic acid), neoprene, nitrile, acrylates such as polyacrylates, poly(2-hydroxy ethyl methacrylate), methyl methacrylate, 2-hydroxyethyl methacrylate, and copolymers of acrylates with N-vinyl pyrrolidone, N-vinyl lactams, acrylamide, polyurethanes and polyacrylonitrile, glucomannan gel, alkyl celluloses, hydroxyalkyl methyl celluloses, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane.

Other suitable non-resorbable materials include, but are not limited to, lightly or highly cross-linked biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. Depending on the amount of crosslinking within the bioresorbable polymers, the degradation time of the polymer can be reduced, thus making the polymer, for the purpose of this application, appear to be non-resorbable over the time frame of the use of the material for this application. In some embodiments, these materials are present in an amount of 5% to 70% by weight or 10% to 40% by weight.

According to another embodiment, the present application provides a method for making a soft tissue wrap. In this method, one obtains human collagen (or collagen from an engineered source to make it compatible with human collagen) and subjects it to an acid suspension. The acid may be selected to degrade undesirable substances, while leaving intact the soft tissue growth factors.

Next one may expose the human collagen to formaldehyde thereby causing the human collagen to cross-link. Then, one forms a sheet from said human collagen.

In this method, preferably, the human collagen has not been exposed to any enzymes that are capable of removing soft tissue growth factors that are associated with the human collagen. Additionally, in some embodiments, it is not exposed to any alkali. Thus, the process allows the soft tissue growth factors to be conserved.

In some embodiments, the sheet is also exposed to a suspension of human collagen. This suspension may have been subjected to conditions that remove certain proteins such as enzymes and/or alkali conditions. Thus, in some embodiments, this suspension does not have proteins conserved, and the suspension of human collagen has no soft tissue growth factors conserved or essentially no soft tissue growth factors conserved.

In some embodiments, the method further comprises applying additional growth factors to the sheet, by e.g., spraying or painting. Alternatively or additionally, in some embodiments, the method further comprises applying nano-hydroxyapatite to the sheet. In further embodiments, the method comprises coating at least one side of the sheet with a sponge or a mesh structure. As persons of ordinary skill in the art will appreciate, it may help to optimize tissue types. This may be accomplished by laying down a film and cross-linking it. The sponge may be formed on the film and any polymer phases would be in the film portion. The polymer may be treated with a plasma (e.g., oxygen or nitrogen) to make it hydrophilic and better able to bind to the collagen film. Additionally, in some embodiments, one may use plasma to treat the finished collagen product. However, the treatment can damage growth and is undesirable in certain applications.

The resulting product may have the porosity and thickness of any the previous embodiments.

The method may further comprise adding at least one therapeutic agent selected from the group consisting of a growth factor, a cytokine, a statin, an anti-inflammatory agent, a steroid, an analgesic, antibiotic, an anti-infiltrating agent, and a combination thereof to the sheet.

The sheets may be rolled, around damaged tissue and molded to that tissue. Thus, the wraps of the present application may be applied by physically covering a portion or all of the tissue to which it is to be applied, including the damaged or deteriorated site and adjacent tissue. In various embodiments, this may be done without the use of a suture or bone screw. Thus, in these embodiments no holes need to be introduced into a bone.

The compositions and methods of the present application can protect the tendon or ligament during the healing process and in some embodiments facilitate healing by the release of growth factors. They also can keep the severed ends of the ligament or tendon in close contact with each other during their healing process and increase the optimization of absorption of growth factors and any additional therapeutic factors.

The soft tissue (e.g., tendons and ligaments) with which the wraps of the present application may be used, can range in size, and in the location in which the present application may be used. For example, the wraps can be used in conjunction with tendons and ligaments associated with the finger, wrist, arm, elbow, shoulder, hip, knee, leg, ankle, foot, toe and neck. As a person of ordinary skill in the art will appreciate, the wrap should have sufficient surface to cover the site of interest while being sufficiently small and sufficiently smooth to minimize the drag on surrounding tissue.

The wrap, which may be a tendon or a ligament repair sheet, may have a height, H, width, W, and length, L. The length and width will vary depending of the location within the body where the sheet will be used. It is anticipated that the length is such that one can place severed ends of torn ligaments or tendons in the middle of the sheet and the sheet will still extend several centimeters on either side of the tendon, ligament, or bone. In some embodiments, the length of the tendon and ligament repair sheet can range from 1 cm to 20 cm or 1 cm to 5 cm or 5 cm to 10 cm or 10 cm to 15 cm or 15 cm to 20 cm. In some embodiments, the width of the tendon and ligament repair sheet is such that one can wrap from about 25% to more than 100%, e.g., 30% to 50%, 50% to 70% or 90% to 110% around the injured tendon or ligament or around the muscle or bone (thus allowing for overlap of the ends of the sheet when wrapped around the injured tendon or ligament). The width can also be such that the tendon and ligament repair sheet wraps around about 60%, about 65%, about 70%, about 75%, about 80%, about 85%, about 90%, about 95%, about 96%, about 97%, about 98%, about 99%, about 100%, about 105%, or about 110% around the torn tendon or ligament.

It is understood that when the injury is located adjacent to where a tendon or ligament attaches to a bone or muscle, one may find it difficult to encircle the muscle or bone with the repair sheet. As such, one may place the repair sheet on part of the muscle and/or bone. In some embodiments, the repair sheet may extend from about 5% to about 60%, or about 15% to about 55%, or about 25% to about 50% around a muscle or bone. In certain embodiments, the sheet's width should be sufficient that there is overlap from one edge over the other edge when wrapped around the injured ligament or tendon. Because the size of tendons and ligaments can vary, in some embodiments, the width of the sheet can range from about 0.5 cm to about 10 cm. In some embodiments, the height, H, of the sheet can range from about 0.5 mm to about 10 mm. The height should be sufficient that the porous layer has enough porous material to allow for the migration and growth of cells and the binding and release of therapeutic agents.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

EXAMPLES

Example 1

Human Collagen Support of Mesenchymal Cell Proliferation

Mesenchymal cell proliferation on a human collagen cell membrane (or sheet) was observed. An in vitro $C_2Cl_2$ mesenchymal cell culture was set up on a collagen membrane. Proliferation was measured through histology and cell proliferation assays.

A review of a histology assay revealed significant proliferation when a human collagen membrane was observed after 24 hours. Measurement was through toluidine blue staining.

A proliferation assay demonstrated greater mesenchymal cell growth on a human collagen membrane than on a bovine collagen membrane. An alamar blue assay was used to evaluate the proliferation rate. (In alamar blue studies, higher absorbance reflects a high proliferation rate.) The results revealed that the mesenchymal cells proliferated at a significantly higher rate (P value 0.009) on a human collagen membrane as opposed to a bovine collagen membrane. The relative absorbances were approximately 2.75 and 1.9.

Example 2

Human Collagen Support Fibroblast Proliferation and Attachment

In order to examine the effect of a human collagen membrane on human fibroblast cell proliferation and attachment, SEM imaging and cell proliferation assays were conducted. A human fibroblast cell culture on collagen model was used.

SEM analysis showed human fibroblasts cultured on a human collagen membrane for three weeks. The extended fibrils showed normal morphology for active fibroblast cells.

Human fibroblast cells grown on a human or a bovine collagen membrane were observed at 24 hours. A luciferase viability assay was used to evaluate the proliferation rate. A higher luciferase activity reflects a higher proliferation rate. Human fibroblast cells proliferated at a significantly higher rate (P value 0.0016) on a human collagen membrane as compared to a bovine collagen membrane. The higher fibroblast proliferation rate in vitro suggests a faster healing rate in vivo. The activity on human collagen was measures at approximately 14,750 and on bovine collagen at approximately 7500.

Example 3

Tendon Repair Experiments

In order to examine the effect of a collagen membrane wrap on tendon healing a tendon Achilles rupture in an Athymic rat model was used. Observations were made at four weeks by evaluation of gross appearance and histology. The analysis was compared to a control tendon.

A tendon Achilles of an Athymic rat was completely cut and immediately sutured. In the testing group, sutured tendons were wrapped with human collagen sheets.

H&E staining was performed of both the control and collagen wrapped tendons. Representative tissue sections were taken from the midsubstance region of the control and collagen wrapped tendons. Observation of the control tendon revealed disorganization and hypercellularity pockets of cell clusters and misaligned collagen fibers, which created defects and voids that suggest scar formation. By contrast, the tendon wrapped tissue showed some areas of high matrix density and improved matrix alignments, in addition to areas of matrix disorganization and hypercellularity. In the control, scar areas represented 11% of the total area, whereas in the tendon wrapped tissue, scarring represented only 5% of the total area.

MicroCT data was also obtained for the tendon Achilles defect. A 2 mm defect was created in the middle region of the tendon Achilles. After 21 days, the experiment was terminated for evaluation. When the defect was not wrapped with a collagen sheet there were indications of delayed healing. When the defect had been wrapped with a collagen membrane, there was evidence of active healing, which appeared as a normal dense area. When the defect had been wrapped with a collagen sheet that had been loaded with IGF1, there were low density areas, which indicated active healing. A control tendon was also observed in which the tendon contained no defect.

Example 4

Structural Collagen Graft

Collagen fibers were presented in a dense and stable structure that provided directional tensile strength suitable for use in applications that require support tensile function.

Procedure:
1. Tissue source. Both human and bovine tissues were used. The human tissue was derived from fascia and tendons (Achilles, Anterior/Posterior). The bovine tissue was derived from the flexor tendon.
2. Fiber process purification. Collagen containing tissue from the tissue sources of (1) was enzyme acid treated and subjected to solvent (IPA and acetone). It was then defatted and de-watered.
3. Dispersion preparation:
    a. 0.75% collagen dispersion was formed using lactic acid. The collagen fibers were obtained from step (2).
    b. The dispersion in lactic acid was subjected to a Waring blender for 3 cycles each at nsec, 6 W, 10 sec, medium, 10 sec, high for each cycle.
    c. A $4^{th}$ cycle was conducted in a manner similar to that of step (b) but with ethyl alcohol added prior to cycle application. Ethyl alcohol was added at 5% ethyl to available dispersion, for example, 50 mg ethyl alcohol to 1 liter or 0.75% solids dispersion.
4. Fiber densification. Collagen dispersions were precipitated in three methods resulting in very similar fiber precipitates.
    a. According to a first method there was a pH adjustment to 4.7 to 5.6 using dilute (0.1N) NaOH solution. Next there was a salt precipitation using NaCl 8% solution, 15 to 30 ml. A collagen 0.75% dispersion was added to a 30.0 to 50.0 ml NaCl solution at 8% salt concentration. Swirling vigorously, both precipitated fibers and managed (somewhat) their orientation.
   b. A second method was mineral precipitation. This technique was nearly the same as "salt precipitation," but in this instance, untreated tap water was used. Thus, 15-30 ml collagen 0.75% dispersion was added to 500-800 ml. tap water. The mineral content in the tap water precipitated the collagen dispersion with the aid of vigorous swirling.
   c. According to a third method, a prepared precipitation method, the collagen dispersion was diluted by a NaOH pH adjustment, using an Erlenmeyer or Beaker flask. A 30 ml of 0.75% collagen dispersion was formed. This was treated with NaOH while swirling to pH 4.6 to 5.7. A precipitate and clear liquid were formed.
5. Fiber orientation. The precipitated fibers were majority oriented by a swirling motion, which caused most forming fibers to align themselves together in the direction of fluid flow. A mandrel was used to retrieve the densified precipitated fibers from the liquid in the Erlenmeyer flask. This procedure further directionally aligned the precipitated collagen fibers. Successful mandrel winding was conducted in 3 mm to 26 mm diameter mandrels composed of polyethylene, PVC and glass.

The fibers being wound on the mandrel were easily picked up on the mandrels and this feature appeared to be modified by pH, with the lowest pH precipitated fibers being "sticky" and easily wound but most difficult to handle and further process (eliminates water/fluid).
   a. To equally distribute precipitated collagen fibers they were swirled in an Erlenmeyer flask at approximately pH 5.2.
   b. A rod mandrel was immersed into the swirling fiber while turning the rod in the same direction as the fiber flowing but faster. The mandrel was pressed to the side of the flask, thereby expressing excess fluid.
   c. The mandrel was withdrawn wrapped with fiber. Excess fluid dripped off of the mandrel.
   d. The mandrel was continuously turned to maintain the precipitated fiber wrap's uniformity.
   e. In order to shape and express fluid the mandrel, with its fiber load, the mandrel was pressed up against a glass/steel, flat or shaped plate, until the desired shape is and elimination or process fluid were achieved.
   f. To dry the material, the oriented fibers were exposed for air drying, vacuum oven and without lyophilization. The ultimate removal from the mandrel must be considered when selecting each process and the mandrel surfaces. (e.g., Teflon).

There are additional product design requirements that may be considered. For example, air drying results in a dense film-like structure. Vacuum drying results in a film-like structure at the mandrel interface with lofty fiber elsewhere. Lyophilization results in lofty fibers throughout and "loftiness" is more controllable.

A frozen fiber wrap that is around a mandrel may be placed on mandrel supports. By changing temperature and volume, lyophilization occurs. It is then dried, oriented, loft controlled, and precipitated so that fibers are formed. The fibers are slide removed from the mandrel. A cylinder that has a 3 mm wall thickness is formed. The interval diameter, which is determined by the selection of the mandrel may range from 3 mm to 26 mm. The cylinder fiber may be orientated or slit for tendon, nerve or vascular grafts, or the cylinder can remain closed for splicing applications. The formed cylinder is a product form for vascular, biliary, and neural grafts. As such, appropriate cross linking can now be applied, or could have been executed in the dispersion "in situ."

There are many potential designs for the wraps of the present application, which may be used as structural collagen grafts. For example, they may be single directionally oriented, dispersion single directionally oriented, bi-directionally oriented or form a bi-directional tube within a tube. The conserved growth factors are attached to the collagen. Once they are detached, they are lost or denatured.

In a single directionally oriented structure, a tube is formed of collagen fibers. The collagen tube may be loaded on an interior structure or coated onto an exterior structure. In embodiments where loading occurs, within the precipitated collagen fibers a collagen foam core is inserted. The composition is the same except that the foam core is usually cross-linked and the deposited fibers are not. This is followed by secondary lyophilization. When the collagen dispersion is coated onto a structure, there may be a single lyophilization and linking process. By essentially "gluing" together collagen, there may be air drying and lyophilization. These structures may, for example, be used as coil plungers for dry sockets or flat oriented for swings.

In dispersion single directionally oriented applications, a collagen tube may be cut or flattened. If cut, a dispersion may be placed on the surface. If flattened, the dispersion may be formed in the cavity. These applications may be used for growth factor delivery and stabilization devices and may, for example, be used for rotator cuff repairs.

Bi-directionally oriented applications can be formed by cutting and unrolling one set of collagen fibers. After removing this first set of fibers from the mandrel, and cutting, unrolling and turning by 90% another set of collagen fibers so that they are oriented perpendicularly to the first set of collagen fibers, one can insert a dispersion coating and/or impregnation material between the two sets of unrolled fibers, assemble the layers (fibers, dispersion and fibers), dry and cross-link them. These structures may, for example, be used in abdominal repair and tendon wrap applications.

The bi-directional tube within tube applications takes first and second collagen tubes, rotates one of the tubes 90 degrees, compresses it and inserts it into the other tube. The interfaces and interspaces are loaded with dispersions; they may be dried and cross-linked. Examples of applications of these structures are rotator cuff and hernia region.

We claim:

1. A soft tissue wrap comprising non-immunogenic collagen and conserved natural growth factors and a second source of human collagen not being cross-linked, wherein said non-immunogenic collagen and conserved natural growth factors are derived from a human or recombinant animal source and said collagen is cross-linked and is in the form of a collagen sheet that is at least 50% porous, the second source of human collagen being disposed in pores of the collagen sheet, and the soft tissue wrap further comprising demineralized bone particles in a weight concentration of 30-45%.

2. The soft tissue wrap of claim 1, wherein the sheet is between 1 mm and 3 mm thick.

3. The soft tissue wrap of claim 1, wherein one or more of said conserved natural growth factors are soft tissue growth factors and the collagen sheet is cross-linked with formaldehyde.

4. The soft tissue wrap of claim 3 further comprising an additional growth factor that is attached to the sheet.

5. The soft tissue wrap of claim 1 wherein the second source of human collagen has had one or more proteins that are associated with it in its naturally occurring state removed.

6. The soft tissue wrap of claim 1 wherein the second source of human collagen has had one or more proteins that are associated with it in its naturally occurring state conserved.

7. The soft tissue wrap of claim 1 further comprising a nano-hydroxyapatite coating.

8. The soft tissue wrap of claim 1 further comprising a mesh structure or a sponge.

9. The soft tissue wrap of claim 8, wherein the mesh structure or sponge is located on only one side of the sheet.

10. The soft tissue wrap of claim 1 further comprising a therapeutic agent selected from the group consisting of a growth factor, a cytokine, a statin, an anti-inflammatory agent, a steroid, an analgesic, antibiotic, an anti-infiltrating agent, and a combination thereof.

11. The soft tissue wrap of claim 9, wherein the sheet is a hydrophilic plasma treated sheet configured to bind with the mesh structure or sponge.

* * * * *